(12) United States Patent
Berge et al.

(10) Patent No.: US 8,088,825 B2
(45) Date of Patent: Jan. 3, 2012

(54) FATTY ACID ANALOGUES FOR THE TREATMENT OF INFLAMMATORY AND AUTOIMMUNE DISORDERS

(75) Inventors: Rolf Berge, Norway (NO); Pal Aukrust, Ridabu (NO)

(73) Assignee: Life Science Nutrition AS, Hovdebygda (NO)

( * ) Notice: Subject to any disclaimer, the term of this patent is extended or adjusted under 35 U.S.C. 154(b) by 0 days.

(21) Appl. No.: 10/416,378

(22) PCT Filed: Nov. 27, 2001

(86) PCT No.: PCT/NO01/00470
§ 371 (c)(1),
(2), (4) Date: Sep. 2, 2003

(87) PCT Pub. No.: WO02/43728
PCT Pub. Date: Jun. 6, 2002

(65) Prior Publication Data
US 2005/0165103 A1 Jul. 28, 2005

(30) Foreign Application Priority Data
Nov. 28, 2000 (NO) .................................. 20006008

(51) Int. Cl.
*A61K 31/20* (2006.01)
(52) U.S. Cl. ........................................ 514/558; 424/489
(58) Field of Classification Search .................. 514/558
See application file for complete search history.

(56) References Cited

U.S. PATENT DOCUMENTS

| | | | |
|---|---|---|---|
| 5,618,955 A | 4/1997 | Mechoulam et al. | |
| 5,846,959 A * | 12/1998 | Medford et al. | 514/165 |
| 6,262,119 B1 | 7/2001 | Ferrante et al. | |
| 6,303,653 B1 | 10/2001 | Bar-Tana | |

FOREIGN PATENT DOCUMENTS

| | | |
|---|---|---|
| DE | 41 20 917 A1 | 1/1993 |
| WO | WO 94/12466 | 6/1994 |
| WO | WO 9611908 A1 * | 4/1996 |
| WO | WO 9703663 A1 * | 2/1997 |
| WO | WO 9738688 A1 * | 10/1997 |
| WO | WO 99/58120 | 11/1999 |
| WO | WO 01/21575 | 3/2001 |

OTHER PUBLICATIONS

Field et al. Lower proportion of CD45R0+ cells and deficient interleukin-10 production by formula-fed infants, compared with human-fed, is corrected with supplementation of long-chain polyunsaturated fatty acid. J Ped Gastr and Nutr.31:291-299; Sep. 2000.*
Breast Cancer reqsearch and Treatment, vol. 45, pp. 229-239 1997, Farzad Abdi-Dezfull et al, "Eicosapentaenoic acid and sulphur substituted fatty acid analogues inhibit the proliferation of human breast cancer cell in culture".

* cited by examiner

*Primary Examiner* — Jake M. Vu
(74) *Attorney, Agent, or Firm* — Casimir Jones SC

(57) ABSTRACT

The present invention relates to fatty acid analogues of the general formula $R_1-[x_i-CH_2]_n—COOR_2$ and in particular to a method of treating inflammatory disorder selected from the group consisting of rheumatoid arthritis, systemic vasculitis, systemic lupus erythematosus, systemic sclerosis, dermatomyositis, and polymyositis; comprising administering to a mammal in need thereof, an effective amount of tetradecylthioaceticacid or tetradecylselenoacetic acid; or a pharmaceutically acceptable salt thereof.

1 Claim, 4 Drawing Sheets

FATTY ACID ANALOGUES FOR THE TREATMENT OF INFLAMMATORY AND AUTOIMMUNE DISORDERS

FIELD OF THE INVENTION

The present invention relates to fatty acid analogues that can be used for the treatment and/or prevention inflammatory disorders. Further, the invention also relates to methods for enhancing the endogenous production of interleukin-10 (IL-10) and suppressing the production of interleukin-2 in mammalian cells or tissues. The invention also relates to a method for inhibiting the proliferation of stimulated peripheral mononuclear cells.

BACKGROUND OF THE INVENTION

Interleukins, interferons, colony stimulating factors and TNFα are examples of a group of diverse multi-functional proteins called cytokines. Cytokines are a class of secreted soluble proteins normally present in very low concentration in a variety of cells. Lymphoid, inflammatory hemopoietic and other cells such as connective tissue cells (e.g. fibroblasts, osteoblasts) secrete a variety of cytokines which regulate the immune, inflammatory, repair and acute phase responses by controlling cell proliferation, differentiation and effector functions. The effects of cytokines are mediated through binding to high affinity receptors on specific cell types.

An important cytokine is IL-10, a 35-40 kDa peptide produced by helper T-cells, B-cells, monocytes, macrophages and other cell types. In vitro, IL-10 has demonstrated immunosuppressive properties as evidenced by its ability to suppress cytokine production including IL-1 and TNFα.

IL-10 also inhibits activation of other inflammatory cytokines, and therefore has potent anti-inflammatory activity.

It has been of recent interest to administer IL-10 in the treatment of certain conditions characterized by excessive IL-1 and TNFα production. Such diseases or conditions include loosening of prosthetic joint implants, inflammation, diabetes, cancer, graft versus host diseases, viral, fungal and bacterial infections, lipopolysaccharide endotoxin shock, diseases of depressed bone marrow function, thrombocytopenia, osteoporosis, spondyloarthropathies, Paget's disease, inflammatory bowel disease, arthritis, osteoarthritis, autoimmune diseases such as rheumatoid arthritis, systemic lupus erythematosus, and connective tissue diseases.

For example, purified IL-10 has been shown in vitro to suppress certain types of viral infections. U.S. Pat. No. 5,665,345 discloses a method for inhibiting replication of the human immunodeficiency virus, retro-viruses, and Kaposi sarcoma in human cells by administering IL-10.

IL-10 has also been suggested for use in the treatment of certain cancers. U.S. Pat. No. 5,570,190 discloses administering exogenous IL-10 to treat mammals suffering from acute myelogenous leukemia and acute lymphocytic leukemia. IL-10 is said to be administered either in the purified or recombinant form and is believed to inhibit the proliferation of acute leukemia blast cells.

Similarly, IL-10 was shown to inhibit bone marrow metastasis in severe combined immunodeficient mice.

The above conventional approaches to treating conditions characterized by excessive IL-1 and TNFα production have been limited to administering exogenous purified or recombinant IL-10 intravenously. Since IL-10 is a protein, it is difficult to infuse intravenously into a mammal because proteins often leach out of solution and bind to the plastic or glass used in intravenous administration sets. Also, proteins are often incompatible and precipitate when mixed with physiological solutions such as dextrose or saline. In addition, oral and topical routes are unavailable for IL-10 administration. The oral route is unavailable because protein is degraded in the gastrointestinal tract.

None of the above approaches suggests enhancing endogenous IL-10 production in mammals for prophylaxis and treatment of diseases or conditions.

Further, it is known that IL-10 is a powerful deactivator of macrophages and T cells, and inadequate production has been implicated in various autoimmune and inflammatory disorders.

SUMMARY OF THE INVENTION

The present study shows that TTA enhance both LPS and PHA stimulated IL-10, and suppress PHA stimulated IL-2 production in PBMC from healthy blood donors. This may have several implications. First, these findings suggest a marked anti-inflammatory net effect of TTA by both enhancing the release of the anti-inflammatory cytokine IL-10 and by suppressing the release of the inflammatory cytokine IL-2. Second, our findings suggest that TTA may modulate both monocyte (i.e. LPS stimulation) and lymphocyte activation (i.e. PHA stimulation). Finally, the in vitro effect of TTA on activated PBMC from healthy blood donors may reflect the situation in various patient populations characterized by enhanced inflammatory activation in vivo. In fact, ex vivo activated PBMC from healthy controls, may represent the relevant target cells for therapeutically intervention in vivo in various inflammatory disorders.

DETAILED DESCRIPTION OF THE INVENTION

Figure 1:
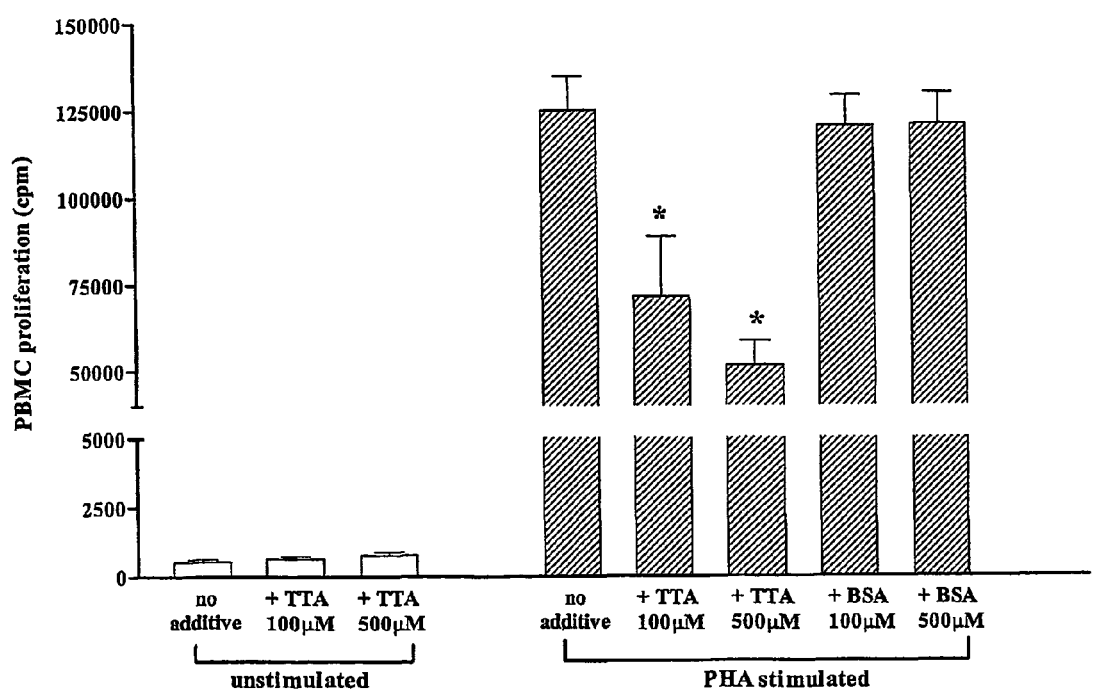
FIG. 1 shows the effect of different concentrations of TTA on proliferation of PBMC.

The present patent application discloses that a preferable compound of the invention, i.e the thia-substituted fatty acid tetradecylthioacetic acid (TTA) modulates the release of inflammatory (i.e. IL-2, IL-1β and TNF-α) and anti-inflammatory (i.e. IL-10) cytokines in the cultured cell line PBMC.

More specifically the present invention discloses that TTA markedly suppresses the PHA stimulated release of IL-2, and also enhances the PHA stimulated release of IL-10.

These two effects adds up to a profound anti-inflammatory effect, and it is thus anticipated that the compounds of the present invention hold promises as interesting compounds for the treatment and/or prevention of disorders related to inflammation.

The present invention thus relates to the use of fatty acid analogues of the general formula (I):

$$R_1\text{-}[x_i\text{-}CH_2]_n\text{---}COOR_2 \qquad (I)$$

wherein $R_1$ is;
- a $C_2$-$C_{24}$ alkene with one or more double bonds and/or with one or more triple bonds, or
- a $C_2$-$C_{24}$ alkyne, or
- a $C_1$-$C_{24}$ alkyl, or a $C_1$-$C_{24}$ alkyl substituted in one or several positions with one or more compounds selected from the group comprising fluoride, chloride, hydroxy, $C_1$-$C_4$ alkoxy, $C_1$-$C_4$ alkylthio, $C_2$-$C_5$ acyloxy or $C_1$-$C_4$ alkyl, and wherein R2 represents hydrogen or $C_1$-$C_4$ alkyl, and wherein n is an integer from 1 to 12, and wherein i is an odd number and indicates the position relative to $COOR_2$, and wherein $X_i$ independent of each other are selected from the group comprising O, S, SO, $SO_2$, Se and $CH_2$, and with the proviso that at least one of the $X_i$ is not $CH_2$, with the proviso that if R1 is an alkyne, then one of the carbon-carbon triple bonds is positioned between the ($\omega$-1) carbon and the ($\omega$-2) carbon, or between the ($\omega$-2) carbon and the ($\omega$-3) carbon, or between the ($\omega$-3) carbon and the ($\omega$-4) carbon, and with the proviso that if R1 is an alkene, then one of the carbon-carbon double bonds is positioned between the ($\omega$-1) carbon and the ($\omega$-2) carbon, or between the ($\omega$-2) carbon and the ($\omega$-3) carbon, or a salt, prodrug or complex thereof, for the preparation of a pharmaceutical composition for the treatment and/or prevention of inflammatory disorders.

More specifically, the invention relates to methods for enhancing the endogenous production of interleukin-10 (IL-10) and suppressing the production of interleukin-2 in mammalian cells or tissues.

The invention also relates to a method for inhibiting the proliferation of stimulated peripheral mononuclear cells Presently preferred embodiments of the present invention relates to the compounds tetradecylthioacetic acid (TTA) and tetradecylselenoacetic acid (TSA).

Administration of the Compounds of the Present Invention

As a pharmaceutical medicament the compounds of the present invention may be administered directly to the mammal by any suitable technique, including parenterally, intranasally, orally, or by absorption through the skin. They can be administered locally or systemically. The specific route of administration of each agent will depend, e.g., on the medical history of the mammal.

In addition, the compounds of the present invention are appropriately administered in combination with other treatments for combating or preventing inflammatory and autoimmune disorders.

The invention will be more fully understood by reference to the following examples. They should not, however, be construed as limiting the scope of the invention.

Example 1

Preparation and Characterisation of the Compounds

The Synthesis of 3-Substituted Fatty Acid Analogues

The compounds used according to the present invention wherein the substituent $X_{i=3}$ is a sulphur atom or selenium atom may be prepared according to the following general procedure:

X is a Sulphur Atom:

The thio-substituted compound used according to the present invention may be prepared by the general procedure indicated below:

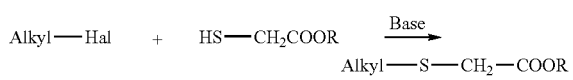

The sulphur-compound, namely, tetradecylthioaceticacid (TTA), ($CH_3$—($CH_2$)$_{13}$—S—$CH_2$—COOH was prepared as shown in EP-345.038.

X is a Selenium Atom:

the seleno-substituted compound used according to the present invention may be prepared by the following general procedure

  1.

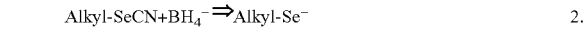  2.

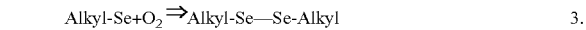  3.

This compound was purified by carefully crystallisation from ethanol or methanol.

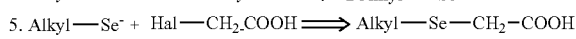

The final compound, e.g. when alkyl is tetradecyl, ($CH_3$—($CH_2$)$_{13}$—Se—$CH_2$—COOH (tetradecylselenoacetic acid (TSA)) can be purified by crystallisation from diethyl ether and hexane.

Other compounds in accordance with the present invention can be synthesised as indicated in applicant's patent applications PCT/NO99/00135 and NO 20001123.

Example 2

Lymphocyte Proliferation

Blood donor (n=5) peripheral blood mononuclear cells (PBMC) were obtained from heparinized blood by Isopaque-Ficoll (Lymphoprep, Nycomed Pharma AS, Oslo, Norway) gradient centrifugation within 1 hour after blood sampling. PBMC were resuspended in RPMI 1640 with 2 mM L-glutamine and 25 mM HEPES buffer (Gibco BRL, Paisley, UK) supplemented with 10% heat inactivated pooled human $AB^+$ serum (culture medium). The endotoxin level in culture medium, reagents and stimulants was <10 pg/mL (Quantitative chromogenic *limulus amebocyte* lysate test, BioWhittaker, Inc., Walkersville, Md.).

PMNC ($10^6$ cells/mL) were incubated in flat-bottomed, 96-well microtiter trays (200 µL/well; Costar, Cambridge, Mass.) in medium alone or with phytohemagglutinin (PHA; Murex Diagnostics Ltd, Dartford, UK; final concentration 1:100) either alone or with different concentrations of TTA. Bovine serum albumin (BSA, Calbiochem, La Jolla, Calif.) was used as a negative control for TTA (vehicle). In some experiments neutralizing monoclonal anti-human interleukin (IL)-10 (final concentration 5 µg/mL; Endogen, Cambridge, Mass.) or recombinant human IL-2 (final concentration 10 ng/mL; R&D Systems, Minneapolis, Minn.) was also added to cell cultures before stimulation. After 48 hours, cells were pulsed with 1 µCi of $^3$H-thymidine (Amersham International plc., Little Chalfont, UK), and 16 hours later cultures were harvested onto glass filter strips, using an automated multisampler harvester (Skatron, Lier, Norway). $^3$H-thymidine incorporation was determined by liquid scintillation counting as counts per minute (cpm).

Results

While TTA had no effect on lymphocyte proliferation when given alone, TTA markedly suppressed PHA stimulated proliferation of PBMC in a dose-dependent manner (~60 reduction; FIG. 1). Such a suppressive effect was seen in all five blood donors. In contrast, no effect on PHA stimulated PBMC proliferation was when the vehicle (BSA) was given alone (FIG. 1).

Example 3

Release of Cytokines in PBMC Supernatants

PBMC ($10^6$ cells/mL) were incubated in flat-bottomed, 96-well microtiter trays (200 μL/well, Costar) in medium alone (see above) or with PHA (final concentration 1:100), lipopolysaccharide (LPS) from *E. coli* 026:B6 (final concentration 10 ng/mL; Sigma, St. Louis, Mo.) or tumor necrosis factor (TNF)? (final concentration 10 ng/mL; R&D Systems) with or without different concentrations of TTA. BSA was used as a negative control for TTA (vehicle). Cell-free supernatants were harvested after 20 hours and stored at −80° C.

Enzyme Immunoassays (EIAs)

Concentration of cytokines in PBMC supernatants were analyzed by EIAs according to the manufacturer's description (IL-1β and IL-10: CLB, Amsterdam, Netherlands; IL-2: R&D Systems).

Statistical Analysis

For evaluation of the effect of TTA (or BSA) on various parameters, the Paired-Samples T Test was used. P-values (two-sided) are considered significant when <0.05.

Results

The Effect of TTA on Cytokine Levels in PBMC Supernatants

Figure 2:
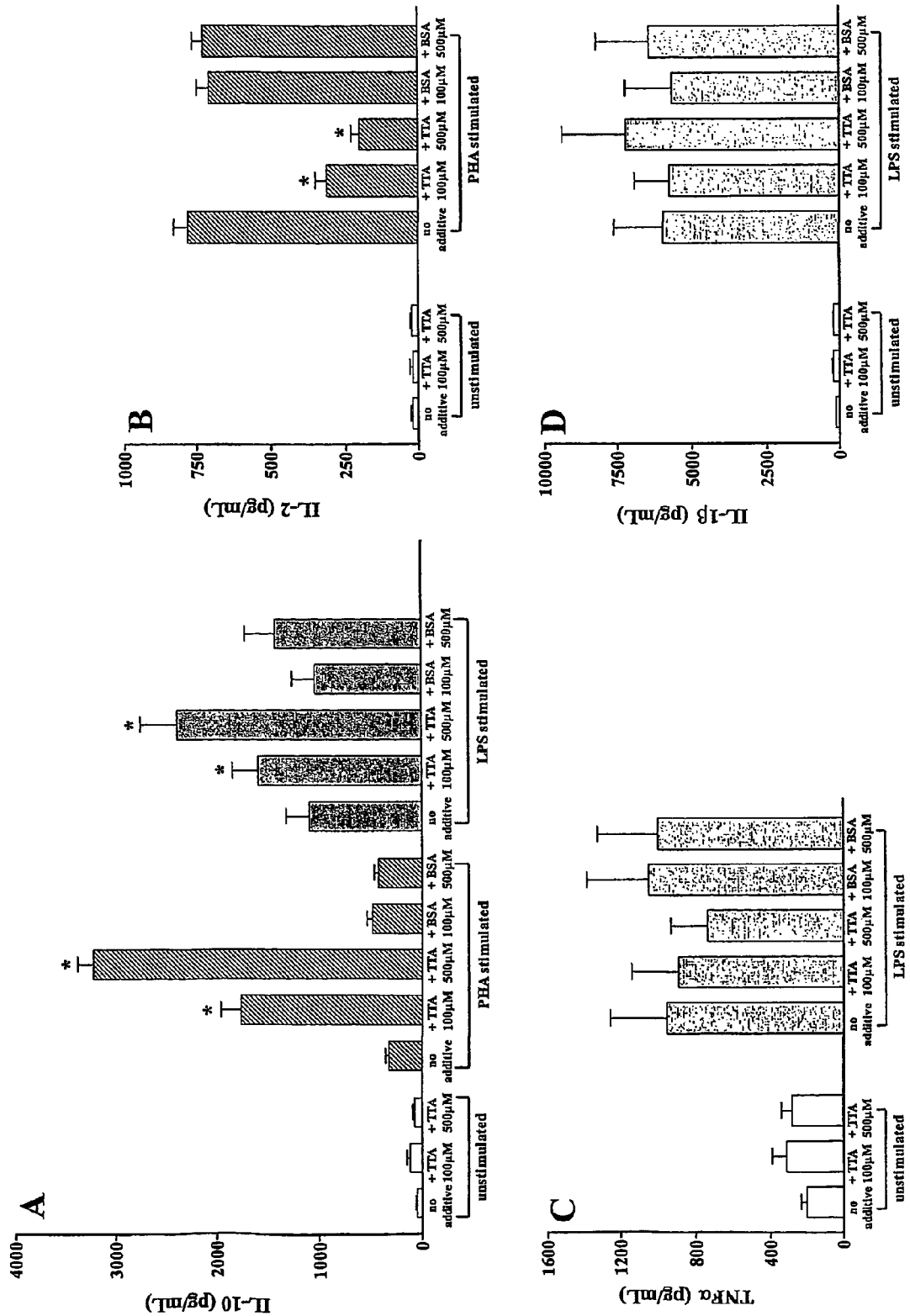
FIG. 2 shows the effect of various concentrations of TTA on the release of IL-10 (A), IL-2 (B), TNFα (C) and IL-1β (D) in PBMC supernatants.

As shown in FIG. 2, TTA alone had no effect on production of either of the cytokines IL-2, IL-1β, IL-10 and TNFα.

However, several significant findings were revealed when TTA were added to cell cultures in combination with PHA or LPS.

First, TTA markedly suppressed the PHA stimulated release of IL-2 in a dose-dependent manner (~75% reduction) (FIG. 2).

Second, in contrast to this suppressive effect, TTA in a dose-dependent manner markedly enhanced both LPS stimulated (~3-fold increase) and in particular PHA stimulated (~11-fold increase) release of the anti-inflammatory cytokine IL-10 (FIG. 2).

Third, in contrast to these pronounced effects on IL-2 and IL-10 levels, TTA had no or only modest effect on LPS stimulated release of TNFα and IL-1β (FIG. 2). There were no effects of the vehicle (BSA) on either PHA or LPS stimulated release of cytokines (FIG. 2).

In conclusion, TTA have several effects on LPS and in particular on PHA stimulated release of cytokines in PBMC favoring anti-inflammatory net effects.

The Effect of TTA on TNFα Stimulated Release of Cytokines in PBMC Supernatants

Figure 3:
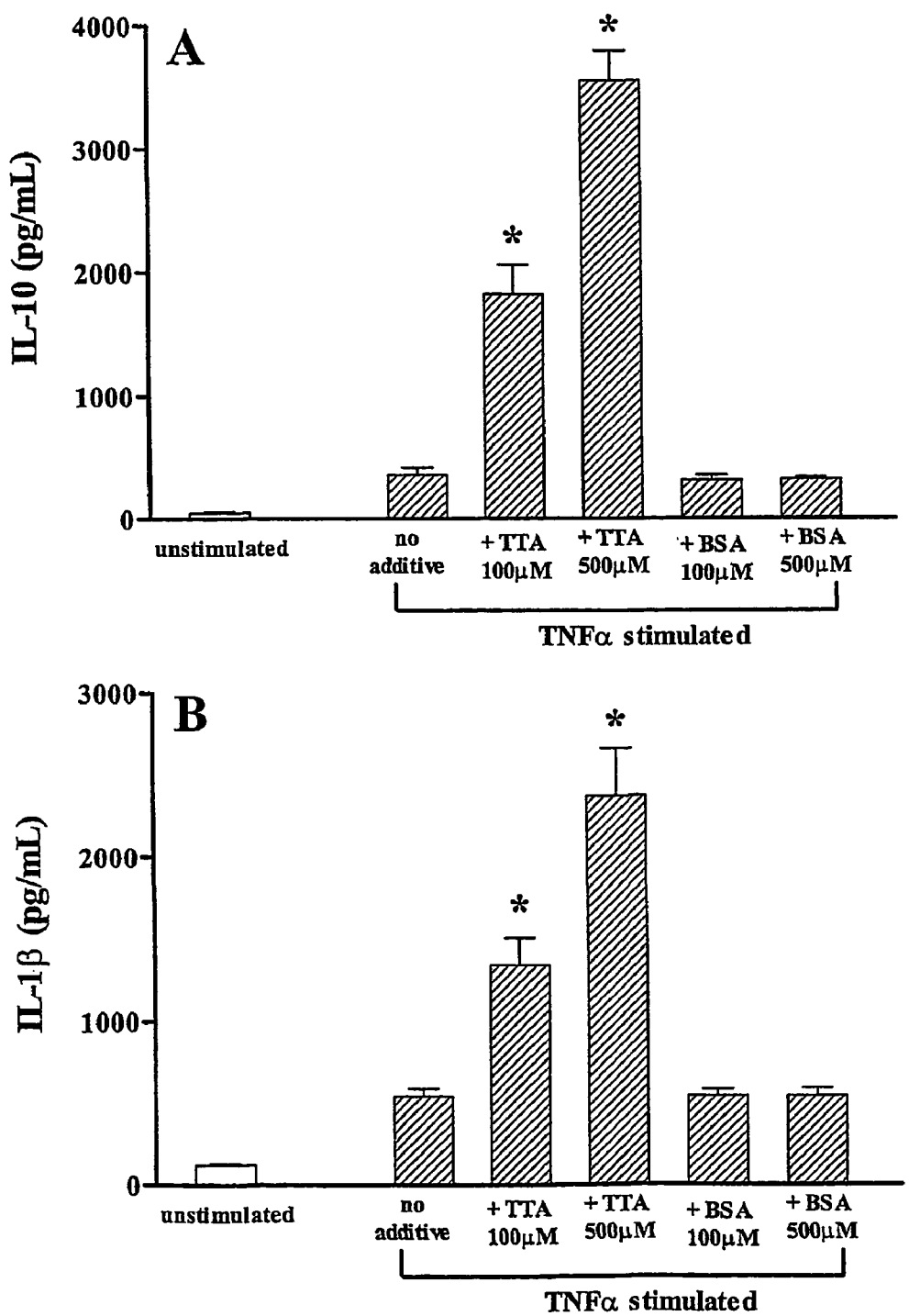
FIG. 3 shows the effect of TNFα (10 ng/mL) alone or in combination with different concentrations of TTA on the release of IL-10 (A) and IL-1β (B) in PBMC supernatants.

Fatty acids have been reported to modulate various TNF mediated effects. TNFα may induce the production of other cytokines such as IL-10 and IL-1β (11,12), and we therefore examined if TTA could modulate the TNFα induced release of these cytokines from PBMC in 5 healthy blood donors. Notably, while TTA had no effect on LPS stimulated release of TNF? (FIG. 2), TTA markedly enhanced the TNFα stimulated release of both IL-1β (~5-fold increase) and in particular of IL-10 (~11-fold increase) (FIG. 3). These findings suggest that TTA can considerably enhance the TNFα stimulated release of cytokines from PBMC with particularly enhancing effect on the release of IL-10.

Example 4

Figure 4:
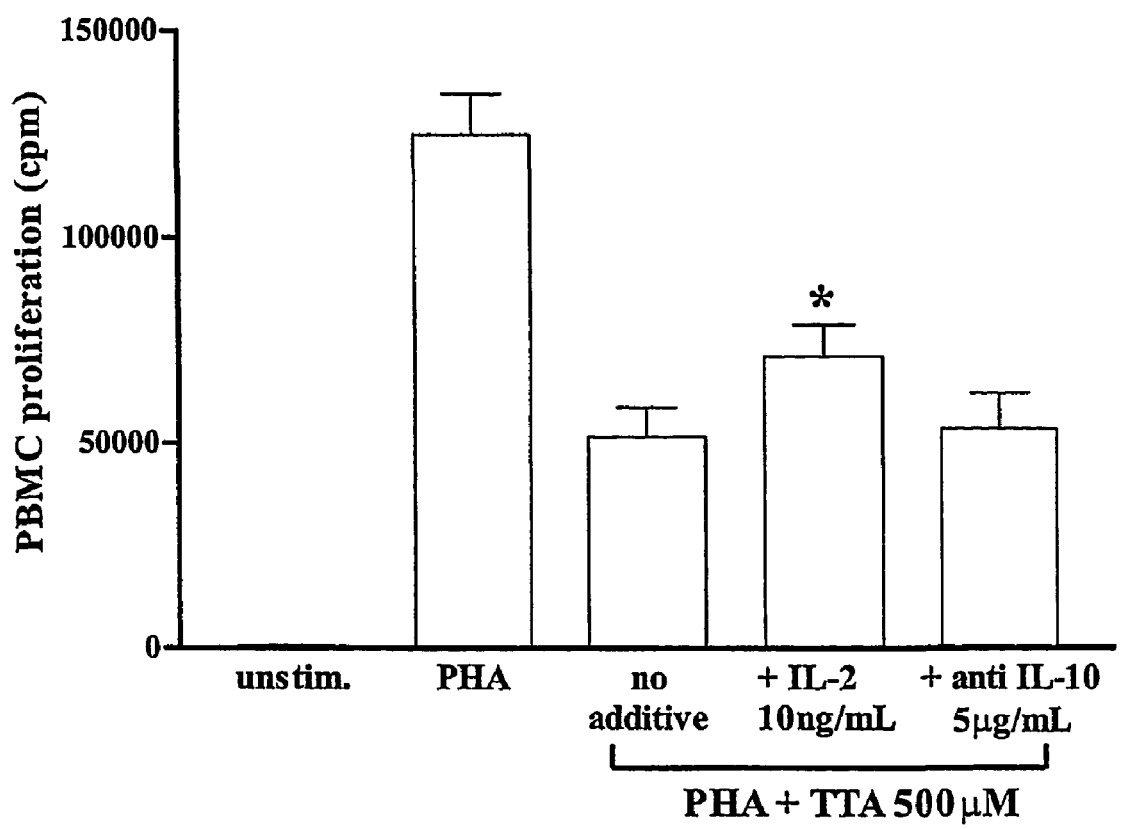
FIG. 4. The effect of IL-2 (10 ng/mL) and anti-IL-10 (5 μg/mL) on the TTA-mediated inhibition of PHA stimulated PBMC proliferation.

Effect of IL-2 and Anti-IL-10 on the TTA Mediated Inhibition of Lymphocyte Proliferation IL-2 and IL-10 is known to enhance and inhibit lymphocyte proliferation, respectively. We therefore examined if the anti-proliferative effect of TTA on PHA stimulated PBMC proliferation was related to the TTA mediated effect on these cytokines (see above). However, the addition of anti-IL-10 to cell cultures had no effect and IL-2 only a modest counteracting effect on the TTA mediated inhibition of lymphocyte proliferation (FIG. 4). Thus, it seems that the anti-proliferative and anti-inflammatory effects of TTA at least partly represent distinct biologic mechanisms.

CONCLUSIONS

As shown in the experimental section TTA has several effects on the release of cytokines from activated PBMC with a marked increase in IL-10 accompanied by a reduction in IL-2 levels. This favors anti-inflammatory net effects, and it is thus anticipated that the compounds of the present invention can be used to regulate inflammatory processes, and thus can be used as medicaments for the treatment and/or prevention of inflammatory disorders.

Further, we have shown that TTA potentates the cytokine stimulating effects of TNFα on these cells with particularly enhancing effect on the IL-10 levels.

Finally, TTA also significantly suppressed PBMC proliferation, and this anti-proliferative effect did not involve enhanced apoptosis and seems at least partly to be distinct from the anti-inflammatory effects of TTA.

Our findings suggest potent anti-inflammatory and anti-proliferative effects of TTA in activated PBMC in humans.

There are several disorders in which enhanced IL-10 and depressed IL-2 levels might be of therapeutically importance. This includes a wide range of immune mediated disorders such as rheumatoid arthritis, systemic vasculitis, systemic lupus erythematosus, systemic sclerosis, dermatomyositis, polymyositis, various autoimmune endocrine disorders (e.g. thyroiditis and adrenalitis), various immune mediated neurological disorders (e.g. multiple sclerosis and myastenia gravis), various cardiovascular disorders (e.g. myocarditis, congestive heart failure, arteriosclerosis and stable and unstable angina, and Wegener's granulomatosis), inflammatory bowel diseases and Chron's colitis, nephritis, various inflammatory skin disorders (e.g. psoriasis, atopic dermatitis and food allergy) and acute and chronic allograft rejection after organ transplantation.

It is known that IL-10 is a powerful deactivator of macrophages and T cells, and inadequate production of IL-10 has been implicated in various autoimmune and inflammatory disorders. It is thus anticipated that the compound of the present invention can be used for the prevention and/or treatment of autoimmune and inflammatory disorders.

Autoimmune models of rheumatoid arthritis, thyroiditis, collagen-induced arthritis and experimental allergic encephalomyelitis all suggest a negatively regulatory role for IL-10 in limiting inflammation and immunopathology. Moreover, mice with a targeted disruption in the IL-10 gene spontaneously develop a generalized enterocolitis. In humans, Chron's colitis and psoriasis may even be susceptible to treatment with systemically administered IL-10. Finally, IL-10 has recently also been found to have protective effects on the development of atherosclerosis and viral myocarditis in mice. Thus, treatment modalities which enhance IL-10 levels may be of great interest in the management of the above mentioned and other autoimmune and inflammatory disorders, and it is contemplated that the compounds of the present invention have such properties.

Further, we have shown that TTA markedly enhanced the TNFα induced IL-10 level, and such anti-inflammatory properties if exploited therapeutically could potentially represent a protection against harmful effect of TNFα.

The invention claimed is:
1. A method of treating inflammatory disorder selected from the group consisting of rheumatoid arthritis, systemic vasculitis, systemic lupus erythematosus, systemic sclerosis, dermatomyositis, and polymyositis; said method comprising administering to a mammal in need thereof, an effective amount of tetradecylthioaceticacid or tetradecylselenoacetic acid; or a pharmaceutically acceptable salt thereof.

* * * * *